(12) United States Patent
Mitchell et al.

(10) Patent No.: US 12,195,729 B2
(45) Date of Patent: *Jan. 14, 2025

(54) PORTABLE FIELD-DEPLOYABLE NUCLEIC ACID SEQUENCING KIT

(71) Applicant: NOBLIS, INC., Reston, VA (US)

(72) Inventors: Shane Mitchell, Reston, VA (US); Masooda Omari, Fairfax, VA (US); Sterling Thomas, Woodbridge, VA (US); Leo Thompson, Sterling, VA (US)

(73) Assignee: NOBLIS, INC., Reston, VA (US)

( * ) Notice: Subject to any disclaimer, the term of this patent is extended or adjusted under 35 U.S.C. 154(b) by 945 days.

This patent is subject to a terminal disclaimer.

(21) Appl. No.: 17/231,280

(22) Filed: Apr. 15, 2021

(65) Prior Publication Data

US 2021/0324371 A1 Oct. 21, 2021

Related U.S. Application Data

(60) Provisional application No. 63/011,022, filed on Apr. 16, 2020.

(51) Int. Cl.
*C12N 15/10* (2006.01)
*B01L 7/00* (2006.01)
*C12Q 1/6806* (2018.01)
*C12Q 1/6869* (2018.01)

(52) U.S. Cl.
CPC ............ *C12N 15/1003* (2013.01); *B01L 7/52* (2013.01); *C12Q 1/6806* (2013.01); *C12Q 1/6869* (2013.01); *B01L 2400/0409* (2013.01)

(58) Field of Classification Search
CPC .............. B01L 2400/0409; B01L 7/52; C12N 15/1003; C12Q 1/6806; C12Q 1/6869
See application file for complete search history.

(56) References Cited

U.S. PATENT DOCUMENTS

| 5,371,665 A * | 12/1994 | Quisenberry ........... F25B 21/02 62/3.3 |
| 2004/0076952 A1* | 4/2004 | Kawai ..................... B01L 7/525 435/6.16 |
| 2014/0358937 A1 | 12/2014 | Thomas et al. |
| 2016/0344849 A1 | 11/2016 | Thomas et al. |
| 2017/0029881 A1* | 2/2017 | Trau ..................... C12Q 1/6851 |
| 2018/0193843 A1* | 7/2018 | Jacobs ..................... B01L 1/52 |
| 2018/0330052 A1 | 11/2018 | Barrus |

(Continued)

OTHER PUBLICATIONS

Yeom ("A Thermocycler Using a Chip Resistor Heater and a Glass Microchip for a Portable and Rapid Microchip-Based PCR Device"). Micromachines 2022, 13, 339. https://doi.org/10.3390/mi13020339 (Year: 2022).*

(Continued)

*Primary Examiner* — Christine T Mui
*Assistant Examiner* — Jonathan Bortoli
(74) *Attorney, Agent, or Firm* — Morrison & Foerster LLP

(57) ABSTRACT

A portable kit for nucleic acid sequencing is disclosed, the kit including a DNA extraction system configured to perform a DNA extraction protocol, a DNA sequencing preparation system configured to perform a DNA sequencing preparation protocol, a sequencer system, and a portable enclosure configured to house the DNA extraction system, the sequencer preparation system, and the sequencer system.

13 Claims, 3 Drawing Sheets

(56) References Cited

U.S. PATENT DOCUMENTS

| | | |
|---|---|---|
| 2018/0330053 A1 | 11/2018 | Ivancich et al. |
| 2018/0330054 A1 | 11/2018 | Omari et al. |
| 2023/0117773 A1 | 4/2023 | Mitchell et al. |

OTHER PUBLICATIONS

Huang ("Low Cost Extraction and Isothermal Amplification of DNA for Infectious Diarrhea Diagnosis"). PLoSONE8(3):e60059. doi: 10.1371/journal.pone.0060059 (Year: 2013).*

Search Manufacturers and Suppliers | Metoree (11 Nucleic Acid Extraction System Manufacturers in 2024) https://us.metoree.com/categories/3791/ (Year: 2024).*

Eppendorf US. "Centrifuge 5425/5425 R—Centrfuges, Centrifugation," located at <https://online-shop.eppendorf.com/OC-en/Centrifugation-44533/Centrifuges-44534/Centrifuge-5425-5425R-PF-934144.html> visited on Apr. 14, 2021. (6 pages).

Qiagen. "DNEasy PowerSoil Pro Kit Handbook," located at <https://www.qiagen.com/us/products/discovery-and-translational-research/dna-rna-purification/dna-purification/microbial-dna/dneasy-powersoil-pro-kit/#orderinginformation> visited on Apr. 1, 2020. (22 pages).

Lapstac Lab Eqipment. "Microcentrifuge CR21," located at <https://web.archive.org/web/20190211102209/http://labstac.com/Microcentrifuge/p/CR121> visited on Feb. 11, 2019. (3 pages).

ThermoFisher Scientific. "Qubit 4 Fluorometer, with Wifi," located at <https://web.archive.org/web/20200603174410if_/https://www.thermofisher.com/order/catalog/product/Q33238#/Q33238> visited on Jun. 3, 2020. (3 pages).

Universal Medical. "Vornado Miniature Vortexer Mixers," located at <https://web.archive.org/web/20201128022705/https://www.universalmedicalinc.com/vornado-miniature-vortexer-mixers.html> visited on Apr. 14, 2021. (7 pages).

Newegg. "ChargeTech Portable Power Supply 54,000 mAh Battery Pack, (2) USB Ports, (2) AC Outlets 250 W 110V (CT60011-PLUG54K," located at <https://www.newegg.com/black-charge-tek-643517490676-54000-mah-power-bank/p/0S8-02UN-00001> visited on Apr. 14, 2021. (3 pages).

Oxford Nanopore Technologies. "About Voltrax," located at <https://web.archive.org/web/20191130212711/https://nanoporetech.com/products/voltrax> visited on Nov. 30, 2019. (5 pages).

Oxford Nanopore Technologies. "MinION," located at <https://web.archive.org/web/20200107064520if_/https://nanoporetech.com/products/minion#> visited on Jan. 7, 2020. (6 pages).

Oxford Nanopore Technologies. "Rapid Lambda Control Experiment (SQK-RAD004)," located at <https://store.nanoporetech.com/us/sample-prep/rapid-sequencing-kit.html#applications_and_publications> visited on Apr. 1, 2020. (4 pages).

Oxford Nanopore Technologies. "Rapid Sequencing Kit," located at <https://store.nanoporetech.com/us/sample-prep/rapid-sequencing-kit.html> visited on Apr. 14, 2021 (2 pages).

Qiagen. "DNeasy PowerSoil Pro Kit," located at <https://www.qiagen.com/us/products/discovery-and-translational-research/dna-ma-purification/dna-purification/microbial-dna/dneasy-powersoil-pro-kit/#/orderinginformation> visited on Apr. 14, 2021. (3 pages).

YouTube. "PowerSoil DNA Isolation Kit Visual Protocol," located at <https://www.youtube.com/watch?=v4ggmR1b0pU> visited on Apr. 5, 2021. (1 page).

* cited by examiner

PORTABLE FIELD-DEPLOYABLE NUCLEIC ACID SEQUENCING KIT

CROSS-REFERENCE TO RELATED APPLICATIONS

This application claims the priority of U.S. Provisional Application No. 63/011,022, filed Apr. 16, 2020, the entire contents of which are incorporated herein by reference.

FIELD OF THE DISCLOSURE

This relates generally to nucleic acid sequencing kits, and more specifically to portable and field-deployable DNA sequencing kits that may be used without internet connection or line power.

BACKGROUND OF THE DISCLOSURE

Sequencing and analysis systems for metagenomics samples require various different specialized laboratory devices. The laboratory equipment required for sequencing and analysis of metagenomics samples is typically expensive, bulky, and immobile, and generally requires a line power connection for power and/or an internet connection for performance of data processing and computations.

SUMMARY OF THE DISCLOSURE

As explained above, sequencing and analysis of metagenomics samples is typically performed using immobile laboratory equipment, such as tabletop laboratory devices, which require line power and/or internet connection in order to operate. Accordingly, sequencing and analysis of metagenomics samples according to known methods requires that samples collected from a field environment be packaged and transported from the field environment to a dedicated laboratory for sequencing and analysis. The transportation from the environment to the dedicated laboratory may be time consuming or entirely impracticable, especially if the environment is in a remote or inaccessible location, the transportation process may increase costs of operations, and the transportation process may introduce risks or damage or compromise the collected sample.

Accordingly, there is a need for systems, methods, and techniques for collection, sequencing, and analysis of metagenomics samples that can be performed in a deployed field environment, without requiring immobile tabletop laboratory equipment.

In some embodiments, a portable field-deployable nucleic acid sequencing kit provides lightweight and portable components for sequencing and analysis of metagenomics samples that do not require internet connection or line power, and that may therefore address the above needs. In some embodiments, a kit may be configured to sequence and analyze metagenomics samples without transporting the samples to a dedicated laboratory that includes specialized equipment. The kit may be deployed for use in an environment with limited resources. For example, the kit may be utilized without internet access or line power. The kit may include components for extracting DNA from a metagenomics sample, preparing the extracted DNA for sequencing, quantifying a concentration of the extracted DNA, and direct sequencing of the extracted DNA prepared for sequencing. The components of the kit may be housed within a portable enclosure.

In some embodiments, the portable kit may be configured to decrease turnaround time between sample collection and analysis. The decreased turnaround time supports real-time surveillance of samples collected from an inaccessible or sensitive field environment.

In some embodiments, a portable kit for nucleic acid sequencing includes: a DNA extraction system configured to perform a DNA extraction protocol; a DNA sequencing preparation system configured to perform a DNA sequencing preparation protocol; a sequencer system; and a portable enclosure configured to house the DNA extraction system, the sequencer preparation system, and the sequencer system.

In any of these embodiments, the kit may include a first centrifuge and a portable power supply, wherein: the first centrifuge is configured to ramp to a target speed at a first ramp rate when drawing power from the portable power supply, and the first centrifuge is configured to ramp to the target speed at a second ramp rate, faster than the first ramp rate, when drawing power from a source of line power.

In any of these embodiments, ramping at the first ramp rate may include increasing from an initial speed to the target speed in predetermined increments.

In any of these embodiments, the sequencer system may include a sequencer device, a heating device positioned external to the sequencing device, and an insulated casing that houses the sequencing device and the heating device.

In any of these embodiments, the kit may include a portable power supply, a mixer, a fluorometer, and a portable computing device, wherein the portable power supply is configured to power the first centrifuge, the second centrifuge, the mixer, fluorometer, and the portable computing device.

In any of these embodiments, the kit may include a portable computing device and a sample preparation device, wherein the portable computing device is configured to control and power a sequencer device of the sequencing system and the sample preparation device.

In some embodiments, a method for DNA sequencing using a portable field kit includes: extracting DNA using DNA extraction tools, a first centrifuge, a second centrifuge, and a mixer included in the portable field kit; quantifying extracted DNA using a fluorometer included in the portable field kit; preparing the extracted DNA for sequencing using the second centrifuge, the mixer, sequencing preparation tools, and a sample preparation device included in the portable field kit; and sequencing the prepared extracted DNA using a sequencing system included in the portable field kit.

In any of these embodiments, the method may include powering the first centrifuge, the second centrifuge, the mixer, the fluorometer, and a portable computing device with a portable power supply included in the portable field kit.

In any of these embodiments, the method may include powering and controlling a sequencer device of the sequencing system and the sample preparation device with the portable computing device included in the portable field kit.

In some embodiments, a method for using a portable kit for DNA extraction includes: executing a first ramping protocol of a first centrifuge included in the kit, the first ramping protocol includes: ramping a first centrifuge to an intermediate speed; operating the first centrifuge at the intermediate speed for a predetermined amount of time without increasing its speed above the intermediate speed; after operating the first centrifuge at the intermediate speed for the predetermined amount of time, ramping the first centrifuge from the intermediate speed to a target speed.

In any of these embodiments, the first centrifuge may be configured to execute the first ramping protocol when the first centrifuge is drawing power from a portable power supply included in the kit; the first centrifuge may be configured to execute a second ramping protocol when the first centrifuge is drawing power from a source of line power, wherein the second ramping protocol includes ramping the first centrifuge directly to the target speed without first operating at the intermediate speed for the predetermined amount of time.

In any of these embodiments, the method may include maintaining a sequencer device included in the kit at an operational temperature using an insulating housing and a heating device included in the kit, wherein the insulating housing and the heating device are positioned external to the sequencer device.

In some embodiments, a kit includes: DNA extraction tools; a first centrifuge and a second centrifuge, the first centrifuge is configured to ramp to a target speed at a first ramp rate when drawing power from the portable power supply, and the first centrifuge is configured to ramp to the target speed at a second ramp rate, faster than the first ramp rate, when drawing power from a source of line power; a mixer; a fluorometer; sequencing preparation tools; a sample preparation device; a sequencing system that includes a sequencing device, a heating device positioned external to the sequencing device, and an insulated casing that houses the sequencing device and the heating device; a portable computing device configured to power and control the sample preparation device and the sequencer; a portable power supply configured to power the first centrifuge, the second centrifuge, the mixer, the fluorometer, and the portable computing device; and a portable enclosure configured to house the DNA extraction tools, the centrifuges, the mixer, the fluorometer, the preparation tools, the sample preparation device, the sequencing system, the portable power supply, and the portable computing device.

In some embodiments, any one or more of the systems, methods, kits, and/or devices described above may be combined, in whole or in part, with all or part of any other one or more of the systems, methods, kits, and/or devices disclosed herein.

BRIEF DESCRIPTION OF THE FIGURES

The invention will now be described, by way of example only, with reference to the accompanying drawings, in which.

DETAILED DESCRIPTION OF THE DISCLOSURE

Figure 1:
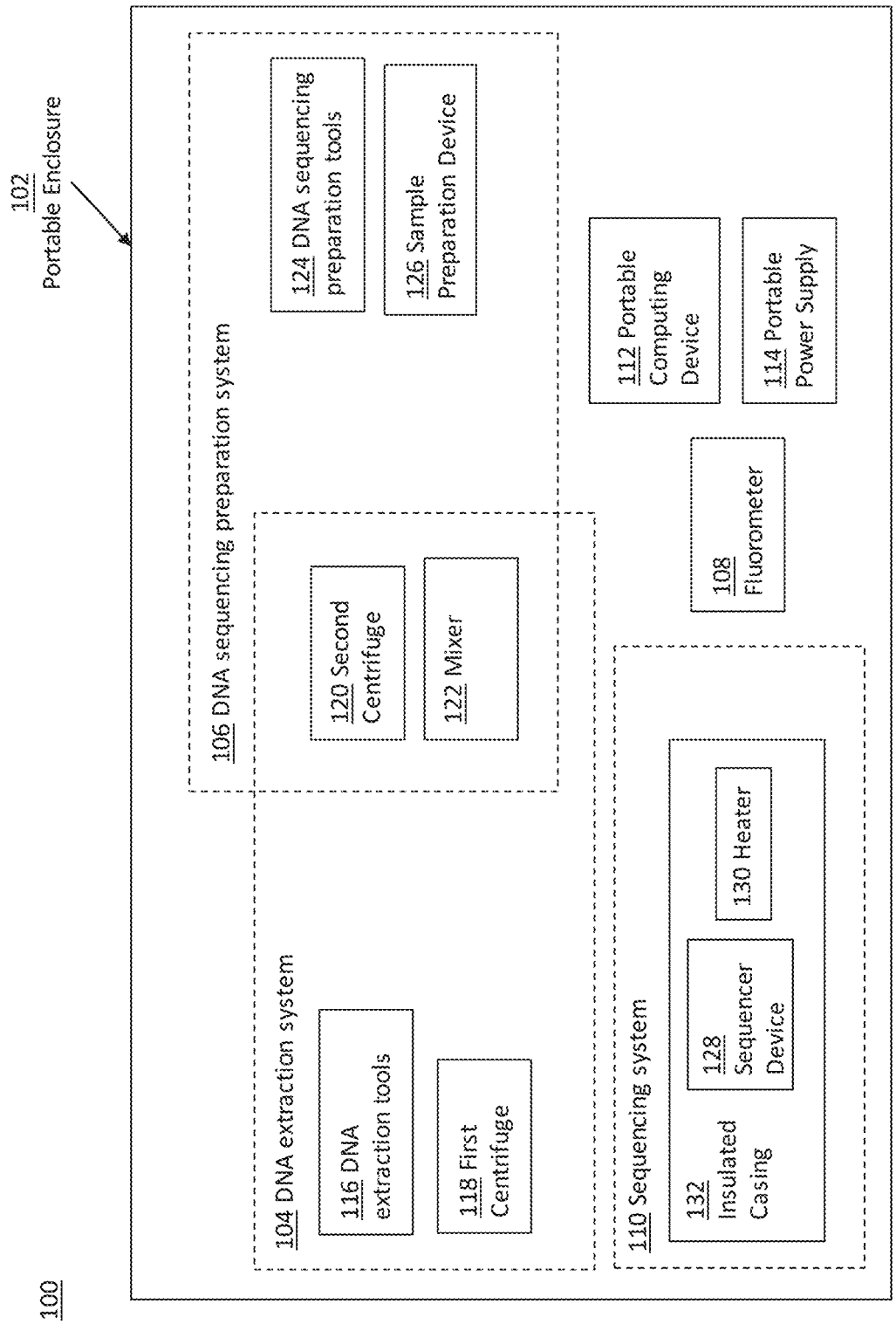
FIG. 1 shows a diagrammatic representation of a portable nucleic acid sequencing kit, in accordance with some embodiments.

In some embodiments, a portable field sequencing kit includes components configured to extract DNA, quantify DNA, and sequence DNA of metagenomics samples. As described herein, the components may include a DNA extraction system, a DNA sequencing preparation system, and a sequencing system, each of which may include one or more subcomponents. The components may include a fluorometer, a portable computing device, and a portable power supply. The portable field sequencing kit may include a casing for housing, transporting, and protecting the various components of the kit as they are transported and deployed in the field.

In some embodiments, the different systems included in the kit include subcomponents such as tools and equipment configured for field sequencing operations. In some embodiments, the DNA extraction system may include DNA extraction tools, a mini centrifuge, a high-G spin centrifuge, and a mixer configured to perform one or more steps of a DNA extraction protocol of the DNA extraction system. In some embodiments, performing the DNA extraction protocol yields extracted DNA from metagenomics sample. In some embodiments, the extracted DNA may be quantified by the fluorometer. In some embodiments, the extracted DNA may be prepared for sequencing via the sequencing preparation system. The sequencing preparation system may include DNA preparation tools and may include a sample preparation device for automating pipetting and manipulation steps of the sequencing preparation system. In some embodiments, the sequencing preparation system may include the mini centrifuge and the mixer. The prepared extracted DNA may then be sequenced via the sequencing system.

In some embodiments, a portable field sequencing kit may be used for extracting DNA via the DNA extraction system, quantifying the extracted DNA via the fluorometer, preparing extracted DNA for sequencing via the sequencing preparation system, and direct sequencing of the extracted DNA via the sequencer system. In some embodiments, the kit may include instructions for doing so, including instructions (e.g., code) for causing one or more electronic components to automatically carry out one or more processes for doing so.

In the following description of the disclosure and embodiments, reference is made to the accompanying drawings in which are shown, by way of illustration, specific embodiments that can be practiced. It is to be understood that other embodiments and examples can be practiced, and changes can be made, without departing from the scope of the disclosure.

In addition, it is also to be understood that the singular forms "a", "an," and "the" used in the following description are intended to include the plural forms as well, unless the context clearly indicates otherwise. It is also to be understood that the term "and/or," as used herein, refers to and encompasses any and all possible combinations of one or more of the associated listed items. It is further to be understood that the terms "includes," "including," "comprises," and/or "comprising," when used herein, specify the presence of stated features, integers, steps, operations, elements, components, and/or units, but do not preclude the presence or addition of one or more other features, integers, steps, operations, elements, components, units, and/or groups thereof.

As shown in FIG. 1, according to some embodiments, a field sequencing kit 100 may include components configured to extract DNA from a sample, prepare extracted DNA for DNA sequencing, and sequence the prepared extracted DNA. In some embodiments, the kit 100 may include a DNA extraction system 104, a DNA sequencing preparation system 106, a fluorometer 108, and a sequencing system 110. In some embodiments, the DNA extraction system 104 may be configured to receive a sample containing DNA and output DNA extracted from the sample. In some embodiments, the fluorometer 108 may be configured to quantify a concentration of the extracted DNA. In some embodiments, the sequencing preparation system 106 may be configured to receive the extracted DNA and prepare the extracted DNA for sequencing. In some embodiments, the sequencing system 110 may be configured to receive the prepared DNA and output sequencing information of the prepared DNA. In some embodiments, the sequencing system 110 may include a sequencer device 128 and a heater 130 housed within an insulated casing 132.

In some embodiments, the field sequencing kit 100 may include one or more power supplies. For example, the field sequencing kit 100 may include a portable computing device 112 configured to power and control the sequencing preparation device 126 and the sequencer device 128. In some embodiments, the field sequencing kit 100 may include a portable power supply 114 configured to power the first centrifuge 118, the second centrifuge 120, the mixer 122, the fluorometer 108, and the portable computing device 112.

In some embodiments, the field sequencing kit 100 may include a portable for enclosure 102 for housing the DNA extraction system 104, the DNA sequencing preparation system 106, the sequencing system 110, the fluorometer 108, the portable computing device 112, and the portable power supply 114.

In some embodiments, the field sequencing kit 100 may be configured for processing RNA. For example, the field sequencing kit 100 may include an RNA extraction system and an RNA sequencing preparation system. The components of the RNA extraction system and the RNA sequencing preparation system may be respectively similar to the DNA extraction system and the DNA sequencing preparation system, sharing one or more characteristics in common therewith. In some embodiments, the RNA systems may include reagents configured for processing RNA and the DNA systems may include reagents configured for processing DNA.

DNA Extraction

In some embodiments, the DNA extraction system 104 may be configured to extract DNA from a sample using DNA extraction tools 116 and equipment 118, 120, 122. The sample may be collected, for example, from soil, compost, manure, water, cell samples, or the like. The sample may contain high humic acid content. The DNA extraction system 104 may be configured to remove factors in the sample that prevent efficient DNA amplification and high-quality DNA purification. In some embodiments, the DNA extraction tools may be a DNeasy® PowerSoil® Pro Kit.

In some embodiments, the DNA extraction system 104 may be configured to perform a DNA extraction protocol for extracting DNA that includes sample preparation, cell lysis, inhibitor removal, DNA binding, DNA washing, and DNA elution. In some embodiments, the DNA extraction protocol includes utilization of DNA extraction tools 116, the first centrifuge 118, the second centrifuge 120, and the mixer 122. In some embodiments, the DNA extraction tools 116 may include a plurality of reagents, each reagent may be configured to facilitate or carry out one or more steps of the DNA extraction protocol. In some embodiments, the DNA extraction tools 116 may include a plurality of tubes for containing the sample. In some embodiments, the DNA extraction tools 116 include one or more spin columns. In some embodiments the reagents may be added in a predetermined sequence to the sample for extracting DNA.

In some embodiments, the first centrifuge may be configured to apply a high G-force to collected samples as part of the DNA extraction system protocol. The high G-force is used to separate contents within a processing tube (such as an Eppendorf tube). In some embodiments, the first centrifuge may have a small footprint and a quiet operation with or without a rotor lid. In some embodiments, the first centrifuge may have a rotor lid configured for fast and ergonomic lid locking. In some embodiments, the first centrifuge may automatically enter into an energy conservative mode after a predetermined amount of time of non-use. The energy conservative mode may reduce energy consumption and extend lifetime of the first centrifuge. In some embodiments, the predetermined amount of time may be at least 4 hours, 6 hours, or 8 hours. In some embodiments, the predetermined amount of time may be at most 14 hours, 12 hours, or 10 hours. In some embodiments, the predetermined amount of time may be 4-14 hours, 6-12 hours, or 8-10 hours.

In some embodiments, the first centrifuge may include a rotor configured to house a plurality of processing tubes. In some embodiments, the rotor may have a maximum rotor capacity of at least 12×1.5/2.0 mL tubes, 14×1.5/2.0 mL tubes, 16×1.5/2.0 mL tubes, 18×1.5/2.0 mL tubes. In some embodiments, the rotor may have a maximum rotor capacity of at most 26×1.5/2.0 mL tubes, 24×1.5/2.0 mL tubes, 22×1.5/2.0 mL tubes, 20×1.5/2.0 mL tubes. In some embodiments, the rotor may have a maximum rotor capacity of a 12-26×1.5/2.0 mL tubes, 14-24×1.5/2.0 mL tubes, 16-22×1.5/2.0 mL tubes, 18-20×1.5/2.0 mL tubes.

In some embodiments, the first centrifuge may have a maximum speed for quick separation. In some embodiments, the maximum speed for quick separation may be at least 10,000 RPM, 12,000 RPM, or 14,000 RPM. In some embodiments, the maximum speed for quick separation may be at most 20,000 RPM, 18,000 RPM, or 16,000 RPM. In some embodiments, the maximum speed for quick separation may be 10,000-20,000 RPM, 12,000-18,000 RPM, or 14,000-16,000 RPM.

In some embodiments, when powered by the portable power supply 114, the first centrifuge 118 may be configured to ramp to a target speed at a predetermined rate that enables the portable power supply 114 to deliver sufficient power for the ramping operation. For example, the predetermined ramping rate may be determined to allow the first centrifuge to increase power at a rate that does not overload the portable power supply 114. In some embodiments, the target speed may be the maximum speed of the first centrifuge.

In some embodiments, the predetermined rate may be slower than a predefined ramp rate preset by a manufacturer of the first centrifuge for line power use (e.g., laboratory use). For example, when the first centrifuge is powered by the portable power supply 114, the minimum programmable ramp preset by the manufacturer of the first centrifuge 118 may overload the portable power supply 114. However, when the first centrifuge 118 is powered by the portable power supply 114, ramping the first centrifuge 118 at the predetermined (e.g., more gradual) rate does not overload the portable power supply 114. In some embodiments, the predetermined rate may include ramping to an initial speed and then ramping from the initial speed to the target speed in one or more increments spaced apart from one another by one or more predetermined intervals. In some embodiments, the initial speed may be at least 1,000 RPM, 1,500 RPM, 2,000 RPM, 2,500 RPM, or 3,000 RPM. In some embodiments, the initial speed may be at most 6,000 RPM, 5,500 RPM, 5,000 RPM, 4,500. RPM, or 4,000 RPM. In some embodiments, the initial speed may be 1,000-6,000 RPM, 1,500-5,500 RPM, 2,000-5,000 RPM, 2,500-4,500 RPM, or 3,000-4,000 RPM. In some embodiments, the increments may be at least 200 RPM, 300 RPM, 400 RPM, or 500 RPM. In some embodiments, the increments may be at most 900

RPM, 800 RPM, 700 RPM, or 600 RPM. In some embodiments, the increments may be 200-900 RPM, 300-800 RPM, 400-700 RPM, or 500-600 RPM.

In some embodiments, the first centrifuge 118 may be configured to control an internal temperature of the first centrifuge 118. The first centrifuge 118 may also be configured to include a quick pre-cooling function inside the rotor. In some embodiments, the first centrifuge 118 may be configured to control the internal temperature of the first centrifuge 118 to at least 0° C., 5° C., 10° C., or 15° C. In some embodiments, the first centrifuge 118 may be configured to control the internal temperature of the first centrifuge 118 to at most 70° C., 60° C., 40° C., or 30° C. In some embodiments, the first centrifuge 118 may be configure to control the internal temperature of the first centrifuge 118 to 0-70° C., 5-60° C., 10-40° C., or 15-30° C.

In some embodiments, the first centrifuge 118 may be configured to control the internal temperature of the first centrifuge 118 to at least 2° C., 3° C., or 4° C. at a maximum rotation speed of the first centrifuge 118. In some embodiments, the first centrifuge 118 may be configured to control the internal temperature of the first centrifuge 118 to at most 7° C., 6° C., or 5° C. at a maximum rotation speed of the first centrifuge 118. In some embodiments, the first centrifuge 118 may be configured to control the internal temperature of the first centrifuge 118 to 2-7° C., 3-6° C., or 4-5° C. at a maximum rotation speed of the first centrifuge 118.

In some embodiments, the first centrifuge 118 may have a low access height of at least 16 cm, 18 cm, 20 cm, or 22 cm. In some embodiments, the first centrifuge may have a low access height of at most 32 cm, 30 cm, 28 cm, or 26 cm. In some embodiments, the first centrifuge may have a low access height of 16-32 cm, 18-30 cm, 20-28 cm, or 22-26 cm.

In some embodiments, the second centrifuge 120 may be a miniaturized centrifuge (e.g., any centrifuge smaller and/or less powerful than the first centrifuge) configured to push liquid reagent stuck to the side of the processing tube towards a bottom of the tube via a spin protocol as part of one or more steps of the DNA extraction system protocol. Compared to a full-sized centrifuge, second centrifuge 120 may have a compact size and may be easier to operate for spinning samples for short spin times. Second centrifuge 120 may be preferred over a full-sized centrifuge for implementing a spin protocol that includes short spin time and does not require a specific g-force. In some embodiments, the short spin time may be at least 1 second or 2 seconds. In some embodiments, the short spin time may be at most 10 seconds, 8 seconds, 5 seconds, or 3 seconds. In some embodiments, the short spin time may be 1-10 seconds, 1-8 seconds, 1-5 seconds, or 1-3 seconds.

In some embodiments, the second centrifuge 120 may be a microfuge. In some embodiments, the second centrifuge 120 may include dynamic braking system. In some embodiments, the second centrifuge 120 may include a direct drive system and/or a vibration drive system. In some embodiments, the second centrifuge 120 may have an automatic speed control. In some embodiments, the second centrifuge 120 may be configured to operate at a constant speed. In some embodiments, the second centrifuge 120 may be configured operate on AC 85V-250V 1 A 50/60 Hz.

In some embodiments, the maximum revolutions per minute (RPM) of the second centrifuge 120 may be at least 5,000 RPM, 6,000 RPM, 7,000 RPM, or 8,000 RPM. In some embodiments, the maximum RPM of the second centrifuge 120 may be at most 10,000 RPM, 9,000 RPM, 8,000 RPM, 7,000 RPM, or 6,000 RPM. In some embodiments, the maximum RPM may be 5,000 RPM-10,000 RPM, 6,000 RPM-9,000 RPM, or 7,000 RPM-8,000 RPM.

In some embodiments, the relative centrifugal force (RCF) of the second centrifuge 120 may be at least 600×g, 700×g, or 800×g. In some embodiments, the RCF of the microfuge may be at most 4,500×g, 4,500×g, or 3,500×g. In some embodiments, the RCF of the microfuge may be 600-4,500×g, 700-4,000 g, or 800-3,500×g.

In some embodiments, the second centrifuge 120 may be configured to accelerate and decelerate. In some embodiments, the second centrifuge 120 may be configured to accelerate to 90% of a rated speed at least within 3 seconds, 4 seconds, or 5 seconds. In some embodiments, the second centrifuge 120 may be configured to accelerate to 90% of a rated speed at most within 7 seconds, 6 seconds, or 5 seconds. In some embodiments, the second centrifuge 120 may be configured to accelerate to 90% of a rated speed within 3-7 seconds, or 4-6 seconds.

In some embodiments, the deceleration of the second centrifuge 120 is based on whether a cover of the second centrifuge 120 is open or closed. In some embodiments, if the cover is open, the second centrifuge 120 may be configured to decelerate at least within 1 second, 2 seconds, or 3 seconds. In some embodiments, if the cover is open, the second centrifuge 120 may be configured to decelerate at most within 6 seconds, 5 seconds, or 4 seconds. In some embodiments, if the cover is open, the second centrifuge 120 may decelerate within 1-6 seconds, 2-5 seconds, or 3-4 seconds.

In some embodiments, if the cover is closed, the second centrifuge 120 may be configured decelerate at least within 10 seconds, 12 seconds, or 14 seconds. In some embodiments, if the cover is closed, the second centrifuge 120 may be configured to decelerate at most within 24 seconds, 22 seconds, or 20 seconds. In some embodiments, if the cover is closed, the second centrifuge 120 may be configured to decelerate within 10-24 seconds, 12-22 seconds, or 14-20 seconds.

In some embodiments, the mixer 122 may be part of one or more steps of the DNA extraction system protocol. In some embodiments, the mixer 122 may be a compact vortex mixer (also known as a vortexer) configured to agitate reagents and ensure homogenous mixing of reagents within processing tubes (such as Eppendorf vials). In some embodiments, electrical conditions of the mixer 122 may include 100 to 240V and 50/60 Hz. In some embodiments, the mixer 122 may have a speed range of 0-4,000 RPM, 0-3,000 RPM, or 0-2,000 RPM.

In some embodiments, the mixer 122 may have a portable size. In some embodiments, the mixer 122 may have a height of at least 1 inches, 2 inches, or 3 inches. In some embodiments, the mixer 122 may have a height of at most 7 inches, 6 inches, of 5 inches. In some embodiments, the mixer 122 may have a height 1-7 inches, 2-6 inches, or 3-5 inches. In some embodiments, the mixer 122 may have a length of at least 6 inches, 7 inches, or 8 inches. In some embodiments, the mixer 122 may have a length of at most 11 inches, 10 inches, or 9 inches. In some embodiments, the mixer 122 may have a length of 6-11 inches, 7-10 inches, or 8-9 inches. In some embodiments, the mixer 122 may have a width of at least 4 inches, 5 inches, or 6 inches. In some embodiments, the mixer 122 may have a width of at most 9 inches, 8 inches, or 7 inches. In some embodiments, the mixer 122 may have a width of 4-9 inches, 5-8 inches, or 6-7 inches.

In some embodiments, the mixer 122 may have a load bearing capacity of at least 0.5 lb or 1 lb. In some embodiments, the mixer 122 may have a load bearing capacity of at most 3.5 lbs or 2.5 lbs. In some embodiments, the mixer 122 may have a load bearing capacity of 0.5-3.5 lbs or 1-2.5 lbs.

In some embodiments, the extracted DNA of the DNA extraction system 104 is purified DNA and may be configured to make DNA of the sample accessible and available for one or more downstream processes such as quantification and sequencing.

DNA Quantification

In some embodiments, a fluorometer 108 may be used to quantify a concentration of eluted DNA from the DNA extraction system 104. In some embodiments, a portion of the eluted DNA may be used for the quantification, and in some embodiments that portion cannot thereafter be sequenced. In some embodiments, the fluorometer 108 may be have a small footprint suitable for a portable fluorometer. In some embodiments, the fluorometer may be a Qubit™ 4 fluorometer.

In some embodiments, the fluorometer 108 may quantify DNA, RNA, and protein at least within 1 second, 2 seconds, 3 seconds, or 4 seconds. In some embodiments, the fluorometer 108 may quantify DNA, RNA, and protein at most within 9 seconds, 8 seconds, 7 seconds, or 6 seconds. In some embodiments, the fluorometer 108 may quantify DNA, RNA, and protein within 1-9 seconds, 2-8 seconds, 3-7 seconds, or 4-6 seconds. In some embodiments, the fluorometer 108 measures intact RNA within at least 2 seconds, 3 seconds, 4 seconds, or 5 seconds. In some embodiments, the fluorometer 108 measures intact RNA within at most 9 seconds, 8 seconds, 7 seconds, or 6 seconds. In some embodiments, the fluorometer 108 measures intact RNA within at most 2-9 seconds, 3-8 seconds, 4-7 seconds, or 5-6 seconds.

In some embodiments, the fluorometer 108 may quantify DNA with small volumes or very dilute samples. In some embodiments, a small volume may be at least 0.5 µL or 1 µL. In some embodiments, a small volume may be at most 40 µL, 30 µL, 20 µL. In some embodiments, a small volume may be 0.5-40 µL, 1-30 µL, or 1-20 µL.

In some embodiments, data associated with DNA quantification may be stored on the fluorometer 108 for at least up to 250 samples, 500 samples, or 750 samples. In some embodiments, the data associated with DNA quantification may be stored on the fluorometer 108 for at most up to 2,000 samples, 1,500 samples, or 1,000 samples. In some embodiments, the data associated with DNA quantification may be stored on the fluorometer 108 for up to 250-2,000 sample, 500-1,500 samples, or 750-1,000 samples.

In some embodiments, the fluorometer 108 may include a user interface that has a color touch screen. The user interface may display graphical data associated with quantification of samples when samples are quantified to be in a predetermined range. In some embodiments, the fluorometer 108 may display content in a plurality of languages such as English, French, Spanish, Italian, German, simplified Chinese, and Japanese. In some embodiments, data from the fluorometer 108 may exported via a WIFI dongle, a USB drive, or via a USB cable.

The fluorometer 108 may be programmable to run assays for DNA quantification. In some embodiments, the fluorometer 108 may include pre-programmed assays. In some embodiments, the fluorometer 108 may be configured to allow a user to program their own assay.

Sequencing Preparation

In some embodiments, the eluted DNA of the extraction system 104 may be processed by the sequencing preparation system 106. In some embodiments, the sequencing preparation system 106 is configured to perform a preparation protocol for generating sequencing libraries from the extracted DNA of the extraction system 104. The preparation protocol may include utilization of the DNA sequencing tools 124, the second centrifuge 120, the mixer 122, and the sample preparation device 126 of the sequencing preparation system 106. In some embodiments, the DNA sequencing tools 124 may include a plurality of reagents, one or more of which may be configured to facilitate one or more steps of the DNA preparation protocol. In some embodiments, the DNA sequencing tools may be a Rapid Sequencing Kit. In some embodiments, the preparation protocol may be a two-step protocol that involves cleaving the eluted DNA molecules and attaching tags to the cleaved ends, and then adding sequence adapters to the tagged ends. In some embodiments, the cleavage is transposase-based. In some embodiments, a read length is a random distribution based on an input fragment length.

In some embodiments, a preparation time of the preparation protocol may be rapid. In some embodiments, the preparation time may be at least 6 minutes, 8 minutes, or 10 minutes. In some embodiments, the preparation time may be at most 16 minutes, 14 minutes, of 12 minutes. In some embodiments the preparation time may be 6-16 minutes, 8-14 minutes, or 10-12 minutes.

In some embodiments, the sequencing preparation system 106 may be configured to process extracted DNA that has or has not undergone polymerase chain reaction (PCR). In some embodiments, if the extracted DNA does not contain a sufficient amount of genetic material for DNA sequencing, then the field sequencing kit 100 may be used to perform PCR. In some embodiments, the sequencing preparation system 106 may process a minimum of 200 ng, 300 ng, or 400 ng of high molecular weight DNA from the extraction system 104. In some embodiments, the sequencing preparation system 106 may process at most 700 ng, 500 ng, or 600 ng of high molecular weight DNA from the extraction system 104. In some embodiments, the sequencing preparation system 106 may process 200-700 ng, 300-500 ng, or 400-600 ng of high molecular weight DNA from the extraction system 104.

In some embodiments, the sample preparation device 126 may be configured to automate one or more protocol steps associated with preparing a sequencing library. Preparation device 126 may be configured to perform a final step of sample preparation (e.g., before sequencing). The protocol may be predefined or a custom sample preparation protocol defined by a user. In some embodiments, the sample preparation device 126 may be configured to automate one or more steps of the sample preparation protocol of the sequencing preparation system 106. For example, the sample preparation device 126 may be configured to replace manual pipetting and manual manipulation steps (such as mixing and separation between reagents) of the sample preparation protocol. The automated sample preparation device 126 may be configured to reduce hands-on sample preparation time and achieve a high level of reproducibility for library preparations.

In some embodiments, the sample preparation device 126 may be a portable, lightweight, robust automated device configured to provide a controlled environment for incubations and extractions. In some embodiments, the sample preparation device 126 may include a metal chassis that includes a heater, a peltier, an optical fluorescent detector and magnets. In some embodiments, the sample preparation device 126 may be a Voltrax V2 device.

In some embodiments, the DNA sequencing preparation system 106 outputs prepared DNA based on the eluted DNA.

The prepared DNA may be configured for processing by the sequencing system 110. For example, the prepared DNA may include attachments (such as transposase and sequencing adapted molecules) that help guide the DNA for sequencing by the sequencing system 110.
Sequencing In some embodiments, the sequencer device 128 of the sequencing system 110 may be configured to receive the prepared DNA of the DNA sequencing preparation system 106. In some embodiments, the sequencer device 128 performs direct sequencing of the prepared DNA and outputs sequencing information. In some embodiments, the sequencer device 128 may be a MinION™.

In some embodiments, the sequencer 128 may include a sample intake, a consumable flow cell, a sensor array, a sensor chip (Application-Specific Integrated Circuit, ASIC), and a USB port. In some embodiments, the sample may be loaded into the sequencer 128 via the sample intake. In some embodiments, the sample may flow through the consumable flow cell and interface with electronics of the sequencer 128. In some embodiments, the sensor array may include a plurality of sensors communicatively connected to a plurality of electrodes. In some embodiments, the plurality of electrodes may be connected to a plurality of channels of a sensor chip (ASIC). The individual channels of the sensor chip (ASIC) may acquire, measure, and control data from the sensor array.

In some embodiments, the USB port of the sequencer device 128 may be configured to connect the sequencer to a portable computing device, a computer, or other device such that the portable computing device, computer, or other device may operate the sequencer device 128.

In some embodiments, the sequencer device 128 may include an onboard heater configured to maintain an operational temperature. In some embodiments, the onboard heater may not be sufficient to maintain the operational temperature in cold conditions, for example, when the air temperature surrounding the sequencer device 128 is less than or equal to about 2° C. In some embodiments, the sequencing system 110 may include an external heater 130 and an insulated casing 132 configured to maintain the operational temperature of the sequencer device 128 when the air temperature is less than or equal to about 2° C.

In some embodiments, the insulated housing 132 may be configured to enclose the sequencer device 128 and the external heater 130. In some embodiments, the insulated casing 132 may have dimensions of at least 9 inches×3 inches×2 inches. In some embodiments, the casing 132 may have dimensions of at most 14 inches×9 inches×8 inches. In some embodiments, the casing 132 may have dimensions of 9-14 inches x 3-9 inches x 2-8 inches. In some embodiments, the insulated box may be made from Styrofoam™.

In some embodiments, the external heater may be a heatwrap positioned about, adjacent, or at a predetermined distance from the sequencer device 128.
Portable Computing Device In some embodiments, the portable computing device 112 may perform computer processing for one or more components of the kit, and may provide power to one or more components from an on-board power supply separate from the external power supply (power supply 114) discussed below. In some embodiments, the portable computing device 112 may be a consumer-grade laptop or tablet device with one or more USB ports for connecting to kit components. For example, the portable computing device 112 may be configured to power and control the sequencer device 128 and the sample preparation device 126 via one or more USB ports. In some embodiments, the portable computing device 112 may be a consumer-grade laptop or tablet.

The portable computing device 112 may be configured to operate software for sequencing, basecalling, and organism identification. For example, the portable computing device 112 may include offline-MinKnow for sequencing, Guppy for basecalling, and Centrifuge for organism identification using a pre-computed reference database.
Power Supply In some embodiments, the portable power supply 114 may be configured to power the first centrifuge 118, the second centrifuge 120, the mixer 122, the fluorometer 108, and the portable computing device 112. In some embodiments the power supply 114 may be a PLUG portable power supply. In some embodiments, the power supply 114 may have a battery capacity of at least 30,000 mAh, 40,000 mAh, or 50,000 mAh. In some embodiments, the battery capacity may be at most, 80,000 mAh, 70,000 mAh, or 60,000 mAh. In some embodiments, the battery capacity may be 30,000-80,000 mAh, 40,000-70,000 mAh, or 50,000-60,000 mAh. In some embodiments, the portable power supply 114 may include a charging port, two international AC outlets, two fast charge USB ports, and one USB type C port. In some embodiments, the power supply 114 may be configured to have 110 V and 220V options.

In some embodiments, the portable power supply 114 may be configured to have dimension of at least 3 inches×6 inches×0.5 inches. In some embodiments, the portable power supply 114 may be configured to have dimension of at most 7 inches×10 inches×3 inches. In some embodiments, the portable power supply 114 may be configured to have dimension of 3-7 inches×6-10 inches×0.5-3 inches.

In some embodiments, one or more portable power supplies may be configured to power equipment in the field and the portable enclosure 102 may be configured to house the one or more portable power supplies.

Figure 2:
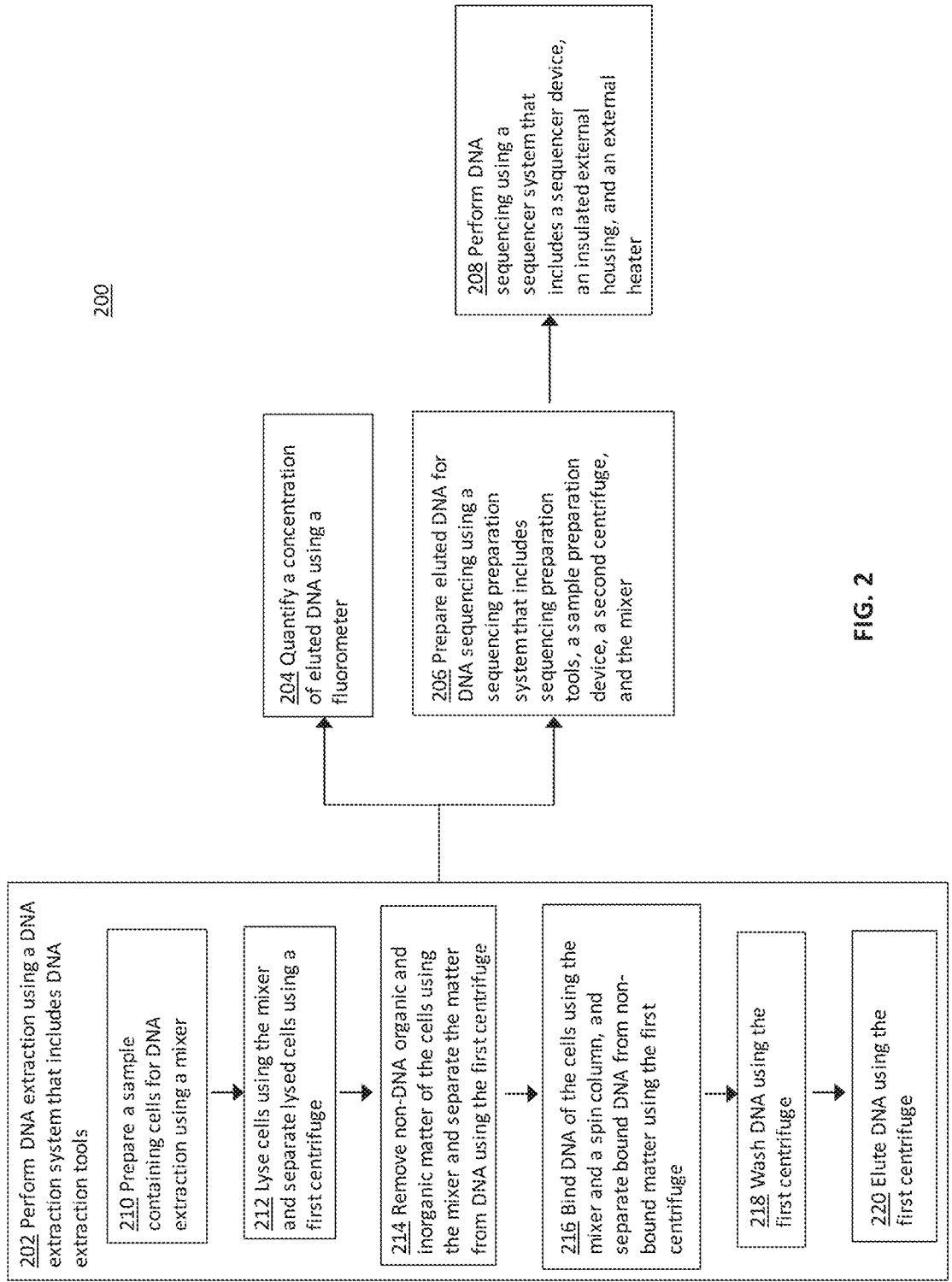
FIG. 2 shows a method for nucleic acid sequencing using a portable nucleic acid sequencing kit, in accordance with some embodiments.

FIG. 2 shows a method 200 for performing nucleic acid sequencing using the portable nucleic acid sequencing kit 100, according to some embodiments. In step 202, a sample containing DNA may be processed by the DNA extraction system (such as extraction system 104). The DNA extraction system may be configured to output eluted DNA. In step 204, the eluted DNA may be quantified by a fluorometer. In step 206, the eluted DNA may be received by the DNA sequencing preparation system (such as preparation system 106). The preparation system may be configured to output DNA prepared for sequencing. In step 208, the sequencing system (such as 110) may be configured to output sequencing data of the extracted DNA.

In some embodiments, step 202 may include a preparation step 210, a lyse step 212, a removal step 214, a binding step 216, a wash step 218, and an elution step 220. In some embodiments, preparation step 210 includes preparing a sample containing cells for DNA extraction using a mixer (such as mixer 122). In some embodiments, the lysis step 212, the removal step 214, and the binding step 216 may include utilization of a mixer and a centrifuge (such as the mixer 11 and the first centrifuge 118). In some embodiments, the wash step 218 and the elution step 220 may include utilization of a first centrifuge (such as the first centrifuge 118).

In some embodiments, step 206 may include utilization of sequencing preparation tools, a sample preparation device, a second centrifuge, and a mixer (such as preparation tools 124, separation device 126, second centrifuge 120, and mixer 122).

In some embodiments, step 208 may include utilization of a sequencer device (such as sequencer device 128) and a heater (such as heater 130) positioned within an insulated casing (such as insulated casing 132).

Figure 3:
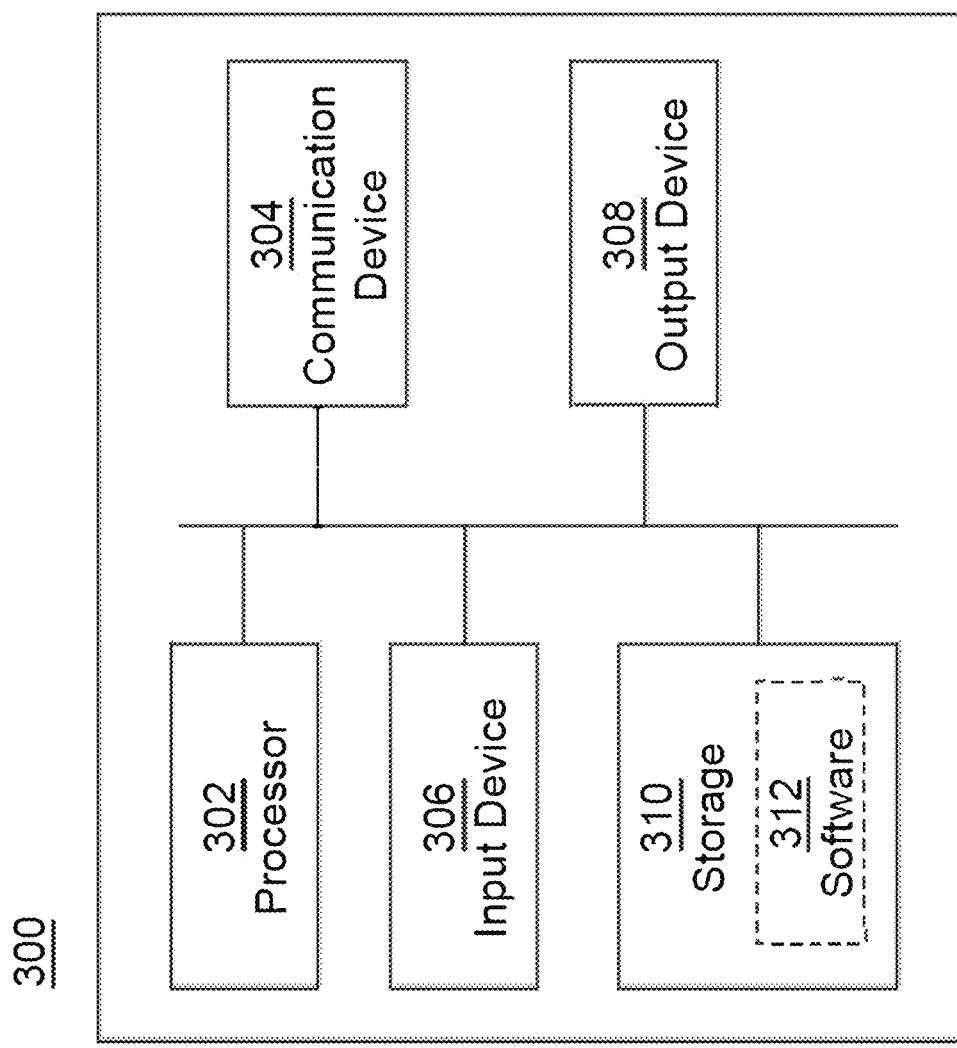
FIG. 3 shows a computer, in accordance with some embodiments.

FIG. 3 depicts an example of a computer system that may be implemented as part of any one or more of the systems, devices, or subcomponents described herein, and that may be configured to perform all or part of any one or more of the methods or techniques described herein, in accordance with some embodiments. As shown in FIG. 3, system 300 can be any suitable type of microprocessor-based device, such as a personal computer, workstation, server, handheld computing device, such as a phone or tablet, or distributed computing system (e.g., cloud computing system). The system can include, for example, one or more of processor 302, communication device 304, input device 306, output device 308, storage 310, and/or software 312 stored on storage 310 and executable by processor 302. The components of the computer can be connected in any suitable manner, such as via one or more physical buses or wirelessly.

In some embodiments, system 300 may include server-side computing components as well as client-side computing components. The specific elements shown in FIG. 3 may, in some embodiments, be included in a server-side computer and/or may, in some embodiments, be included in a client-side computer. In some embodiments, system 300 may include server-side components and client-side components that are in communication with one another via one or more instances of communication device 304, which may, for example, enable communication of server-side components and client-side components over a network connection.

In some embodiments, some or all components of system 300 may be part of a distributed computing system (e.g., a cloud computing system). In some embodiments of the techniques disclosed herein, for example, storage 310 may be storage provisioned by a cloud computing system, such that a user may send instructions to the cloud computing system over one or more network connections, and the cloud computing system may execute the instructions in order to leverage the cloud computing components in accordance with the instructions. In some embodiments, cloud computing systems may be configured to be capable of executing the same or similar program code in the same programming languages as other systems (e.g., servers, personal computers, laptops, etc.) as discussed herein.

Processor 302 may be any suitable type of computer processor capable of communicating with the other components of system 300 in order to execute computer-readable instructions and to cause system 300 to carry out actions in accordance with the instructions. For example, processor 300 may access a computer program (e.g., software 312) that may be stored on storage 310 and execute the program to cause the system to perform various actions in accordance with the program. In some embodiments, a computer program or other instructions executed by processor 302 may be stored on any transitory or non-transitory computer-readable storage medium readable by processor 302.

Communication device 304 may include any suitable device capable of transmitting and receiving signals over a network, such as a network interface chip or card. System 300 may be connected to a network, which can be any suitable type of interconnected communication system. The network can implement any suitable communications protocol and can be secured by any suitable security protocol. The network can comprise network links of any suitable arrangement that can implement the transmission and reception of network signals, such as wireless network connections, T1 or T3 lines, cable networks, DSL, or telephone lines.

Input device 306 may be any suitable device that provides input, such as a touch screen or monitor, keyboard, mouse, button or key or other actuatable input mechanism, microphone, and/or voice-recognition device, gyroscope, camera, or IR sensor. Output device 308 may be any suitable device that provides output, such as a touchscreen, monitor, printer, disk drive, light, speaker, or haptic output device.

Storage 310 can be any suitable device that provides storage, such as an electrical, magnetic or optical memory including a RAM, cache, hard drive, CD-ROM drive, tape drive, or removable storage disk.

Software 312, which may be stored in storage 310 and executed by processor 302, may include, for example, the programming that embodies the functionality of the methods, techniques, and other aspects of the present disclosure (e.g., as embodied in the computers, servers, devices, components, and/or subcomponents as described above). In some embodiments, software 312 may include a combination of servers such as application servers and database servers.

Software 312 can also be stored and/or transported within any computer-readable storage medium for use by or in connection with an instruction execution system, apparatus, or device, such as those described above, that can fetch instructions associated with the software from the instruction execution system, apparatus, or device and execute the instructions. In the context of this disclosure, a computer-readable storage medium can be any medium, such as storage 310, that can contain or store programming for use by or in connection with an instruction execution system, apparatus, or device.

Software 312 can also be propagated within any transport medium for use by or in connection with an instruction execution system, apparatus, or device, such as those described above, that can fetch instructions associated with the software from the instruction execution system, apparatus, or device and execute the instructions. In the context of this disclosure, a transport medium can be any medium that can communicate, propagate, or transport programming for use by or in connection with an instruction execution system, apparatus, or device. The transport readable medium can include, but is not limited to, an electronic, magnetic, optical, electromagnetic, or infrared wired or wireless propagation medium.

System 300 can implement any one or more operating systems suitable for operating on the network. Software 312 can be written in any one or more suitable programming languages, such as C, C++, Java, or Python. In various embodiments, application software embodying the functionality of the present disclosure can be deployed in different configurations, such as in a client/server arrangement or through a Web browser as a Web-based application or Web service, for example.

Although the description herein uses terms first, second, etc., to describe various elements, these elements should not be limited by the terms. These terms are only used to distinguish one element from another.

The terminology used in the description of the various described embodiments herein is for the purpose of describing particular embodiments only and is not intended to be limiting. As used in the description of the various described embodiments and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, integers, steps, operations, elements, and/or components but do not preclude the presence or addition of one or more other features, integers, steps, operations, elements, components, and/or groups thereof.

The term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

The foregoing description, for purpose of explanation, has been described with reference to specific embodiments. However, the illustrative discussions above are not intended to be exhaustive or to limit the disclosure to the precise forms disclosed. Many modifications and variations are possible in view of the above teachings. The embodiments were chosen and described in order to best explain the principles of the techniques and their practical applications. Others skilled in the art are thereby enabled to best utilize the techniques and various embodiments with various modifications as are suited to the particular use contemplated.

Although the disclosure and examples have been fully described with reference to the accompanying figures, it is to be noted that various changes and modifications will become apparent to those skilled in the art. Such changes and modifications are to be understood as being included within the scope of the disclosure and examples as defined by the claims.

This application discloses several numerical ranges in the text and figures. The numerical ranges disclosed inherently support any range or value within the disclosed numerical ranges, including the endpoints, even though a precise range limitation is not stated verbatim in the specification, because this disclosure can be practiced throughout the disclosed numerical ranges.

The foregoing description, for the purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the techniques and their practical applications. Others skilled in the art are thereby enabled to best utilize the techniques and various embodiments with various modifications as are suited to the particular use contemplated.

Although the disclosure and examples have been fully described with reference to the accompanying figures, it is to be noted that various changes and modifications will become apparent to those skilled in the art. Such changes and modifications are to be understood as being included within the scope of the disclosure and examples as defined by the claims. Finally, the entire disclosure of the patents and publications referred to in this application are hereby incorporated herein by reference.

The invention claimed is:

1. A portable kit for sequencing nucleic acid from a sample, the portable kit comprising:

a DNA extraction system configured to extract DNA from a sample using a DNA extraction protocol;

a DNA sequencing preparation system configured to prepare the extracted DNA using a DNA sequencing preparation protocol;

a sequencer system including a sequencer device, a heating device, and an insulated casing enclosing the sequencer device and the heating device wherein the sequencer device is surrounded by air, the heating device is external to the sequencer device, and the insulated casing and the heating device are configured to maintain an operational temperature of the sequencer device when a temperature of the air surrounding the sequencer device is less than or equal to about 2° C.; and a portable enclosure enclosing the DNA extraction system, the DNA sequencing preparation system, and the sequencer system.

2. The portable kit of claim 1 further comprising a first centrifuge and a portable power supply, wherein: the first centrifuge is configured to draw power from the portable power supply and from a source line power wherein the first centrifuge ramps to a target speed at a first ramp rate when drawing power from the portable power supply, and wherein the first centrifuge ramps to the target speed at a second ramp rate, faster than the first ramp rate, when drawing power from the source of line power.

3. The portable kit of claim 2, wherein the first centrifuge ramps at the first ramp rate from an initial speed to the target speed in predetermined increments.

4. The portable kit of claim 1 further comprising a first centrifuge, a second centrifuge, a portable power supply, a mixer, a fluorometer, and a portable computing device, wherein the portable power supply is configured to power the first centrifuge, the second centrifuge, the mixer, the fluorometer, and the portable computing device.

5. The portable kit of claim 1 further comprising a portable computing device and a sample preparation device, wherein the portable computing device is configured to control and to power the sequencer device of the sequencing system and the sample preparation device.

6. A method of sequencing DNA from a sample using a portable field kit comprising a DNA extraction system to extract DNA from a sample using a DNA extraction protocol;

a DNA sequencing preparation system to prepare the extracted DNA using a DNA sequencing preparation protocol;

a sample preparation device;

a first centrifuge;

a second centrifuge;

a mixer;

a fluorometer;

a sequencer system including a sequencer device, a heating device, and an insulated casing wherein the sequencer device is surrounded by air, the heating device is external to the sequencer device, and the insulated casing and the heating device are configured to maintain an operational temperature of the sequencer device when a temperature of the air surrounding the sequencer device is less than or equal to about 2° C.; and a portable enclosure enclosing the DNA extraction system, the DNA sequencing preparation system, and the sequencer system, the method comprising:

extracting DNA from the sample using the DNA extraction system, the first centrifuge, the second centrifuge, and the mixer;

quantifying the extracted DNA using the fluorometer;

preparing the extracted DNA for sequencing using the second centrifuge, the mixer, the DNA sequencing preparation system, and the sample preparation device; and sequencing the prepared extracted using the sequencer system.

7. The method of claim 6 wherein the portable field kit further comprises a portable power supply, the method further comprising powering the first centrifuge, the second centrifuge, the mixer, the fluorometer, and a portable computing device using the portable power supply.

8. The method of claim 6 wherein the portable field kit further comprises a portable computing device, the method further comprising powering and controlling the sequencer device of the sequencer system and the sample preparation device with the portable computing device.

9. A method of ramping a plurality of centrifuges using a portable kit comprising:
   a DNA extraction system to extract DNA from a sample using a DNA extraction protocol;
   a DNA sequencing preparation system to prepare the extracted DNA using a DNA sequencing preparation protocol;
   a sample preparation device;
   a first centrifuge;
   a second centrifuge;
   a mixer;
   a fluorometer;
   a sequencer system including a sequencer device, a heating device, and an insulated casing wherein the sequencer is surrounded by air, the heating device is external to the sequencer device, and the insulated casing and the heating device are configured to maintain an operational temperature of the sequencer device when a temperature of the air surrounding the sequencer device is less than or equal to about 2° C.; and
   a portable enclosure enclosing the DNA extraction system, the DNA sequencing preparation system, and the sequencer system, the method comprising:
   ramping the first centrifuge to an intermediate speed by executing a first ramping protocol of the first centrifuge included in the kit;
   operating the first centrifuge at the intermediate speed for a predetermined amount of time without increasing its speed above the intermediate speed; and
   after operating the first centrifuge at the intermediate speed for the predetermined amount of time, further ramping the first centrifuge from the intermediate speed to a target speed wherein the intermediate speed is lower than the target speed.

10. The method of claim 9, wherein the portable kit further comprises a portable power supply and the ramping of the first centrifuge by executing the first protocol is performed with the first centrifuge drawing power from the portable power supply, the method further comprising ramping the first centrifuge using a second ramping protocol wherein the first centrifuge draws power from a source of line power
   wherein the second ramping protocol comprises ramping the first centrifuge directly to the target speed without first operating at the intermediate speed for the predetermined amount of time.

11. The method of claim 9, further comprising maintaining the sequencer device included in the kit at an operational temperature by using the insulating casing and the heating device included in the kit.

12. The portable kit of claim 2, wherein the first centrifuge is configured to control an internal temperature of the first centrifuge.

13. The portable kit of claim 2, wherein the first centrifuge is configured to perform a quick pre-cooling function.

* * * * *